United States Patent
Mueller et al.

(10) Patent No.: US 7,368,274 B2
(45) Date of Patent: May 6, 2008

(54) **EXPRESSION OF RECOMBINANT PROTEINASE K FROM *TRITIRACHIUM ALBUM* IN YEAST**

(75) Inventors: Rainer Mueller, Penzberg (DE); Johann-Peter Thalhofer, Weilheim (DE); Frank Geipel, Penzberg (DE); Stephan Glaser, Seeshaupt (DE); Werner Hoelke, Penzberg (DE); Helmut Schoen, Penzberg (DE); Thomas Kirschbaum, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 494 days.

(21) Appl. No.: 10/468,252

(22) PCT Filed: Feb. 5, 2002

(86) PCT No.: PCT/EP02/01144

§ 371 (c)(1),
(2), (4) Date: Apr. 5, 2004

(87) PCT Pub. No.: WO02/064760

PCT Pub. Date: Aug. 22, 2002

(65) Prior Publication Data

US 2004/0166560 A1    Aug. 26, 2004

(30) Foreign Application Priority Data

Feb. 9, 2001    (DE) ................ 101 05 911

(51) Int. Cl.
*C12N 15/57* (2006.01)
*C12N 9/58* (2006.01)

(52) U.S. Cl. .............. 435/223; 435/320.1; 435/254.23; 536/23.2

(58) Field of Classification Search ............... None
See application file for complete search history.

(56) References Cited

FOREIGN PATENT DOCUMENTS

| EP | 0396106 | 11/1990 |
|---|---|---|
| WO | WO 87/02673 | 5/1987 |
| WO | WO 88/07581 | 10/1988 |
| WO | WO 96/28556 | 9/1996 |

OTHER PUBLICATIONS

1998 INVITROGEN Catalog "The Pichia Expression System" pp. 19-23.*
Clark, Elaina De Bernardez et al., "Inhibition of Aggregation Side Reactions during in Vitro Protein Folding," Methods in Enzymology, vol. 309, pp. 217-236 (1999).
Ebeling, Wolfgang et al., "ProteinaseK from *Tritirachium album* Limber," Eur. J. Biochem., 47, 91-97 (1974).
Gunkel, F. Andreas et al., "Proteinase K from *Tritirachium album* Limber," Eur. J. Biochem. 179-185-194 (1989).
Kane, James F. et al., "Effects of rare codon clusters on high-level expression of heterologous proteins in *Escherichia coli*," Current Opinion in Biotechnology 1995, 6:494-500.
Penheiter, Alan R. et al., "Purification and Characterization of a Soybean Root Nodule Phosphatase Expressed in *Pichia pastoris*," Protein Expression and Purification 14, 125-130 (1998).
Samal, Babru et al., "Cloning and Expression of the Gene Encoding a Novel Proteinase from *Tritirachium album* Limber," Practical Protein Engineering, 1996, pp. 95-104.
Cregg, J. et al., "Recombinant Protein Expression in *Pichia pastoris*," Mol. Biotechnol. vol. 16, No. 1, (2000). 23-52.
Roy, N. et al., "Expression of Human Gelatinase B in *Pichia pastoris*, " Protein Expression and Purification, 16(1999) 324-330.
Borg-von Zepelin, M. et al., "The Expression of the Secreted Aspartyl Proteinases Sap4 to Sap6 from *Candida albicans* in Murine Macrophages," Mol. Microbiol. vol. 28, No. 3, (1998) 543-554.
Hiroshi Nakakubo, et al., "Secretory Production of Recombinant Human Chymase as an Active Form in *Pichia pastoris*, " Yeast 16(2000) 315-323.
Withers-Martinez, C. et al., "PCR-based Gene Synthesis As An Efficient Approach For Expression Of The A + T-rich Malaria Genome," Protein Eng. vol. 12, No. 12(1999), 1113-1120.
Hiroshi Nakakubo et al., "Functional Reconstitution of an Active Recombinant Human Chymase From *Pichia pastoris* Cell Lysate," Yeast 16 (2000), 1387-1396.

* cited by examiner

*Primary Examiner*—Rebecca E. Prouty
(74) *Attorney, Agent, or Firm*—Barnes & Thornburg LLP

(57) ABSTRACT

The invention concerns a method for the expression of a gene coding for a soluble proteinase K in yeast e.g. in *Pichia pastoris* with subsequent secretion into the culture medium. In addition a method for purifying the heterologously expressed and secreted proteinase K is described.

8 Claims, 2 Drawing Sheets

EXPRESSION OF RECOMBINANT PROTEINASE K FROM *TRITIRACHIUM ALBUM* IN YEAST

The present invention concerns a method for the production of recombinant proteinase K in a soluble and active form in economically relevant amounts.

Proteinase K (E.C. 3.4.21.64, also known as endopeptidase K) is an extracellular endopeptidase which is synthesized by the fungus *Tritirachium album* Limber. It is a member of the class of serine proteases with the typical catalytic triad Asp$^{39}$-His$^{69}$-Ser$^{224}$ (Jany, K. D. et al. (1986) *FEBS Letters* Vol. 199(2), 139-144). Since the sequence of the polypeptide chain of 279 amino acids in length (Gunkel, F. A. and Gassen, H. G. (1989) *Eur. J. Biochem.* Vol. 179(1), 185-194) and the three dimensional structure (Betzel, C. et al. (1988) *Eur. J. Biochem.* Vol. 178(1), 155-71) has a high degree of homology to bacterial subtilisins, proteinase K is classified as a member of the subtilisin family (Pahler, A. et al. (1984) *EMBO J.* Vol. 3(6), 1311-1314; Jany, K. D. and Mayer, B. (1985), *Biol. Chem. Hoppe-Seyler*, Vol. 366(5), 485-492). Proteinase K was named on the basis of its ability to hydrolyse native keratin and thus allows the fungus to grow on keratin as the only source of carbon and nitrogen (Ebeling, W. et al. (1974) *Eur. J. Biochem.* Vol. 47(1), 91-97). Proteinase K has a specific activity of more than 30 U/mg and is thus one of the most active of the known endopeptidases (Betzel, C. et al. (1986) *FEBS Lett.* Vol. 197(1-2), 105-110) and unspecifically hydrolyses native and denatured proteins.

Proteinase K from *Tritirachium album* Limber is translated in its natural host as a preproprotein. The sequence of the cDNA of the gene which codes for proteinase K was decoded in 1989 by Gunkel, F. A. and Gassen, H. G. (1989) *Eur. J. Biochem.* Vol. 179(1), 185-194. According to this the gene for prepro-proteinase K is composed of two exons and codes for a signal sequence of 15 amino acids in length, a prosequence of 90 amino acids in length and a mature proteinase K of 279 amino acids in length. A 63 bp intron is located in the region of the prosequence. The prepeptide is cleaved off during translocation into the endoplasmatic reticulum (ER). At present very little is known about the subsequent processing to form mature proteinase K with cleavage of the propeptide.

Consequently mature proteinase K consists of 279 amino acids. The compact structure is stabilized by two disulfide bridges and two bound calcium ions. This explains why proteinase K compared to other subtilisins has a considerably higher stability towards extreme pH values, high temperatures, chaotropic substances and detergents (Dolashka, P. et al. (1992) *Int. J. Pept. Protein. Res.* Vol. 40(5), 465-471). Proteinase K is characterized by a high thermostability (up to 65° C., Bajorath et al. (1988), *Eur. J. Biochem.* Vol. 176, 441-447) and a wide pH range (pH 7.5-12.0, Ebeling, W. et al. (1974) *Eur. J. Biochem.* Vol. 47(1), 91-97). Its activity is increased in the presence of denaturing substances such as urea or SDS (Hilz, H. et al. (1975) *J. Biochem.* Vol. 56(1), 103-108; Jany, K. D. and Mayer, B. (1985) *Biol. Chem. Hoppe-Seyler*, Vol. 366(5), 485-492).

The above-mentioned properties make proteinase K of particular interest for biotechnological applications in which an unspecific protein degradation is required. Special examples are nucleic acid isolation (DNA or RNA) from crude extracts and sample preparation in DNA analysis (Goldenberger, D. et al. (1995) *PCR Methods Appl.* Vol. 4(6), 368-370; U.S. Pat. No. 5,187,083; U.S. Pat. No. 5,346,999). Other applications are in the field of protein analysis such as structure elucidation.

Proteinase K is obtained commercially in large amounts by fermentation of the fungus *Tritirachium album* Limber (e.g. CBS 348.55, Merck strain No. 2429 or the strain ATCC 22563). However, in this process the production of proteinase K is suppressed by glucose or free amino acids. Since protein-containing media also induce the expression of proteases, it is necessary to use proteins such as BSA, milk powder or soybean flour as the only nitrogen source. The secretion of the protease starts as soon as the stationary phase of growth is reached (Ebeling, W. et al. (1974) *Eur. J. Biochem.* Vol. 47(1), 91-97).

Since *Tritirachium album* Limber is consequently unsuitable for fermentation on a large scale and moreover is difficult to genetically manipulate, various attempts have been made to overexpress recombinant proteinase K in other host cells. However, no significant activity was detected in these experiments due to lack of expression, formation of inactive inclusion bodies or problems with the renaturation (Gunkel, F. A. and Gassen, H. G. (1989) *Eur. J. Biochem.* Vol. 179(1), 185-194; Samal, B. B. et al. (1996) *Adv. Exp. Med. Biol.* Vol. 379, 95-104).

*Tritirachium album* Limber is a slowly growing fungus which only secretes small amounts of proteases into the medium. It has the disadvantage of a slower cell cycle compared to yeast and the lower optical density that can be achieved in a fermenter. In addition it is known that *T. album* also produces other proteases apart from proteinase K which can contaminate the preparation (Samal, B. B. et al. (1991) *Enzyme Microb. Technol.* Vol. 13, 66-70).

Although in principle it is possible to express proteinase K in *E. coli*, it is not expressed in a soluble form but in so-called inclusion bodies from which the enzyme has to be subsequently solubilized and renatured by certain measures. A disadvantage of this method is that a lot of protein is lost during the solubilization and renaturing.

Hence the object of the present invention is to provide a method for producing recombinant proteinase K in economically relevant amounts.

It has surprisingly turned out that it is possible to express and secrete recombinant proteinase K as a zymogenic precursor in a soluble form in yeast which is autocatalytically activated to form active proteinase K. Another subject matter of the invention is the purification of active proteinase K from the medium supernatant.

Hence the present invention concerns a method for producing recombinant proteinase K comprising the steps:
a) transformation of a host cell with a vector containing a DNA coding for the zymogenic precursor of proteinase K which is fused upstream of the coding sequence with a sequence in the reading frame which codes for a signal peptide and is under the control of a suitable promoter for the host cell,
b) expression of the zymogenic precursor of proteinase K
c) secretion and autocatalytic activation of proteinase K
d) isolation and purification of proteinase K, characterized in that the host cell is a yeast cell and the protein is secreted in a soluble form by this expression host.

In a special embodiment of the method according to the invention the host cell is selected from the following group: *Pichia* species, *Hansenula* species such as *Hansenula polymorpha*, *Saccharomyces* species, *Schizosaccharomyces* species, *Yarrowia* species such as *Yarrowia lipolytica*, *Kluyveromyces* species and *Aspergillus* species. It is particularly preferred according to the invention when *Pichia pastoris* is used as the host cell.

Furthermore it has proven to be advantageous for the method according to the invention when the host cell is transformed with a DNA coding for the zymogenic precursor and the proteinase K is autocatalytically activated at a later time during or immediately after secretion into the culture medium.

When using *Pichia pastoris* as a host cell, the gene coding for the zymogenic precursor of proteinase K is preferably cloned into the following vectors: pPICZ, pPICZα, pGAPZ, pGAPZα, pPICZαA and pPIC9K. In this case the vectors: pPICZαA and pPIC9K are particularly preferred. According to the invention the vector pPICZαA is particularly preferred. The above-mentioned vectors are commercially available (Invitrogen).

In addition in the inventive method for producing recombinant proteinase K it is preferred that the expression of proteinase K or the zymogenic precursor of proteinase K is induced by methanol (pPIC vectors). Another method is to induce the expression by glyceraldehyde phosphate (pGAP vectors).

In the inventive method for producing recombinant proteinase K the secretion of the protein is preferably initiated by the N-terminal fusion of the signal peptide of the α-factor from *Saccharomyces cerevisiae*. This for example means that the above-mentioned α-labelled vectors have the nucleotide sequence for the signal peptide of the α-factor from *Saccharomyces cerevisiae*. A fusion protein consisting of the signal peptide at the N-terminus and the target protein is then produced during translation. Another possible signal peptide would be the natural signal sequence for proteinase K.

Furthermore it has proven to be particularly advantageous for the production of recombinant proteinase K, to transform the host cell *Pichia pastoris* with the expression vectors pPICZαA and pPIC9K which contain a DNA coding for the zymogenic precursor and that the gene is under the control of the AOX1 promoter and optionally of the AOX1 terminator.

The present invention also concerns a vector containing a DNA coding for the zymogenic precursor of proteinase K which is fused upstream of the coding sequence with a sequence in the reading frame which codes for a suitable signal peptide and wherein the coding gene is under the control of a suitable promoter and optionally terminator for the host cell and wherein this vector is suitable for the transformation of this host cell. According to the invention the host cell is a yeast.

Hence the invention also concerns a recombinant vector which contains one or more copies of the recombinant DNA defined above. The vector is preferably a plasmid which has a strong promoter for the host cell and a suitable signal peptide for the host cell for secreting proteins. Moreover it is also possible to fuse the native signal peptide of preproproteinase K to the N-terminus of the propeptide as shown in SEQ ID NO.: 21 (signal sequence 1-15 (15 amino acids); prosequence 16-104 (90 amino acids); sequence of the mature proteinase K 106-384 (279 amino acids)). Methods are used to produce the expression vector which are familiar to a person skilled in the art and are described for example in Sambrook et al. (1989).

Another subject matter of the present invention is a host cell transformed with one of the vectors listed above where the host cell is a yeast. The host cell is preferably selected from the following group: *Pichia* species, *Hansenula* species such as *Hansenula polymorpha*, *Saccharomyces* species, *Schizosaccharomyces* species, *Yarrowia* species such as *Yarrowia lipolytica*, *Kluyveromyces* species and *Aspergillus* species. *Pichia pastoris* is particularly preferred as the host cell. In particular it is preferred when several vectors (each with one copy of the ppK gene) are integrated into the genome.

In addition the present invention concerns a method for purifying proteinase K. In order to purify the protease the yeast cells are removed in a first step by microfiltration or centrifugation. The resulting clear solution contains the protease. This is followed by a rebuffering by means of ultrafiltration in order to bind the product to a cation exchanger such as SP-Sepharose or SP-Sephadex (Pharmacia) or SP-Toyopearl (Tosoh Corporation). After the elution it is again rebuffered by means of ultrafiltration and bound to an anion exchanger such as DEAE-Sepharose or Q-Sepharose (Pharmacia) or DEAE-Fraktogel (Merck). After another elution the pure protease is transferred by means of ultrafiltration into a stable buffer system (Protein Purification, Principles and Practice, Robert K. Scopes, Springer Verlag, 1982). However, a person skilled in the art can use other methods of purification which are part of the prior art.

The method according to the invention surprisingly enables the preparation of recombinant proteinase K in which the enzyme is produced by a heterologous host cell in a soluble and active form. The expression of proteinase K with subsequent secretion of the enzyme into the culture medium is of particular advantage since it prevents proteinase K from developing a strongly toxic effect in the cytosol of the host cell. Furthermore this ensures the correct formation of the two disulfide bridges which could not readily occur in the reducing environment of the cytosol. Hence an important advantage of the method according to the invention is that it provides an approach for the soluble and active production of a recombinant proteinase K. It is very surprising and inexplicable that the surface proteins of the host cells according to the invention are not hydrolysed by a secreted proteinase K. Such an expected hydrolysis of the surface proteins by proteinase K would interfere with the life cycle of the host cell.

A proteinase K is obtained by the method according to the invention which is homogeneous and hence particularly suitable for analytical and diagnostic applications. The zymogenic precursor of proteinase K according to the invention can optionally contain additional N-terminal modifications and in particular sequences which facilitate purification of the target protein (affinity tags). In addition the zymogenic precursor can contain sequences which increase the efficiency of translation, which increase the folding efficiency and/or also sequences which result in a secretion of the target protein into the culture medium (natural presequence and other signal peptides).

Proteinase K in the sense of the invention means the sequence according to Gassen et al. (1989) shown in SEQ ID NO:1 as well as other variants of proteinase K from *Tritirachium album* Limber like the amino acid sequence disclosed by Ch. Betzel et al. (Biochemistry 40 (2001), 3080-3088) and in particular proteinase T (Samal, B. B. et al. (1989) Gene Vol. 85(2), 329-333; Samal, B. B. et al. (1996) Adv. Exp. Med. Biol. Vol. 379, 95-104) and proteinase R (Samal, B. B. et al. (1990) Mol. Microbiol. Vol. 4(10), 1789-1792; U.S. Pat. No. 5,278,062) and in addition variants produced by recombinant means (as described for example in WO 96/28556). SEQ ID NO:1 comprises a prosequence (1-90; 90 amino acids) and the sequence of the mature proteinase K (91-368; 279 amino acids). The proteinase K amino acid sequence described by Betzel et al. (Biochemistry 40 (2001), 3080-3088) has in particular aspartate instead of a serine residue at position 207 of the active protease.

Pro-proteinase K in the sense of the invention means in particular a proteinase K whose N-terminus is linked to its prosequence according to SEQ ID NO: 1. In the case of subtilisin E which is closely related to proteinase K and variants thereof, the prosequence has an important influence on the folding and formation of active protease (Ikemura, H. et al. (1987) *J. Biol. Chem.* Vol. 262(16), 7859-7864). In particular it is postulated that the prosequence acts as an intramolecular chaperone (Inouye, M. (1991) *Enzyme* Vol. 45, 314-321). After the folding it is processed to form the mature subtilisin protease by autocatalytically cleaving the propeptide (Ikemura, H. and Inouye, M. (1988) *J. Biol. Chem.* Vol. 263(26), 12959-12963). This process occurs in the case of subtilisin E (Samal, B. B. et al. (1989) *Gene* Vol. 85(2), 329-333; Volkov, A. and Jordan, F. (1996) *J. Mol. Biol.* Vol. 262, 595-599), subtilisin BPN' (Eder, J. et al. (1993) *Biochemistry* Vol. 32, 18-26), papain (Vernet, T. et al. (1991) *J. Biol. Chem.* Vol. 266(32), 21451-21457) and thermolysin (Marie-Claire, C. (1998) *J. Biol. Chem.* Vol. 273(10), 5697-5701).

Only certain core regions of the prosequence which are usually hydrophobic appear to be necessary for the chaperone function since a wide range of mutations have no influence on the activity (Kobayashi, T. and Inouye, M. (1992) *J. Mol. Biol.* Vol. 226, 931-933). In addition it is known that propeptides can be interchanged between various subtilisin variants. Thus for example subtilisin BPN' also recognizes the prosequence of subtilisin E (Hu, Z. et al. (1996) *J. Biol. Chem.* Vol. 271(7), 3375-3384).

Hence the present invention concerns the prosequence according to SEQ ID NO:1 of 90 amino acids in length as well as other variants which facilitate folding. It also concerns a propeptide which is added exogenously for the folding of mature proteinase K and has the functions described above.

Hence an important advantage of the method according to the invention is that the recombinant proteinase K is secreted by an expression host into the culture medium in a soluble and active form. Moreover the expression host used in the method according to the invention is not damaged or otherwise impaired by the very active and unspecific protease i.e. in particular it continues to grow without problems and an increased cell lysis is not observed. Furthermore the expression host according to the invention is easier to handle compared to *Tritirachium album* and is characterized by higher growth rates.

Figure 1:
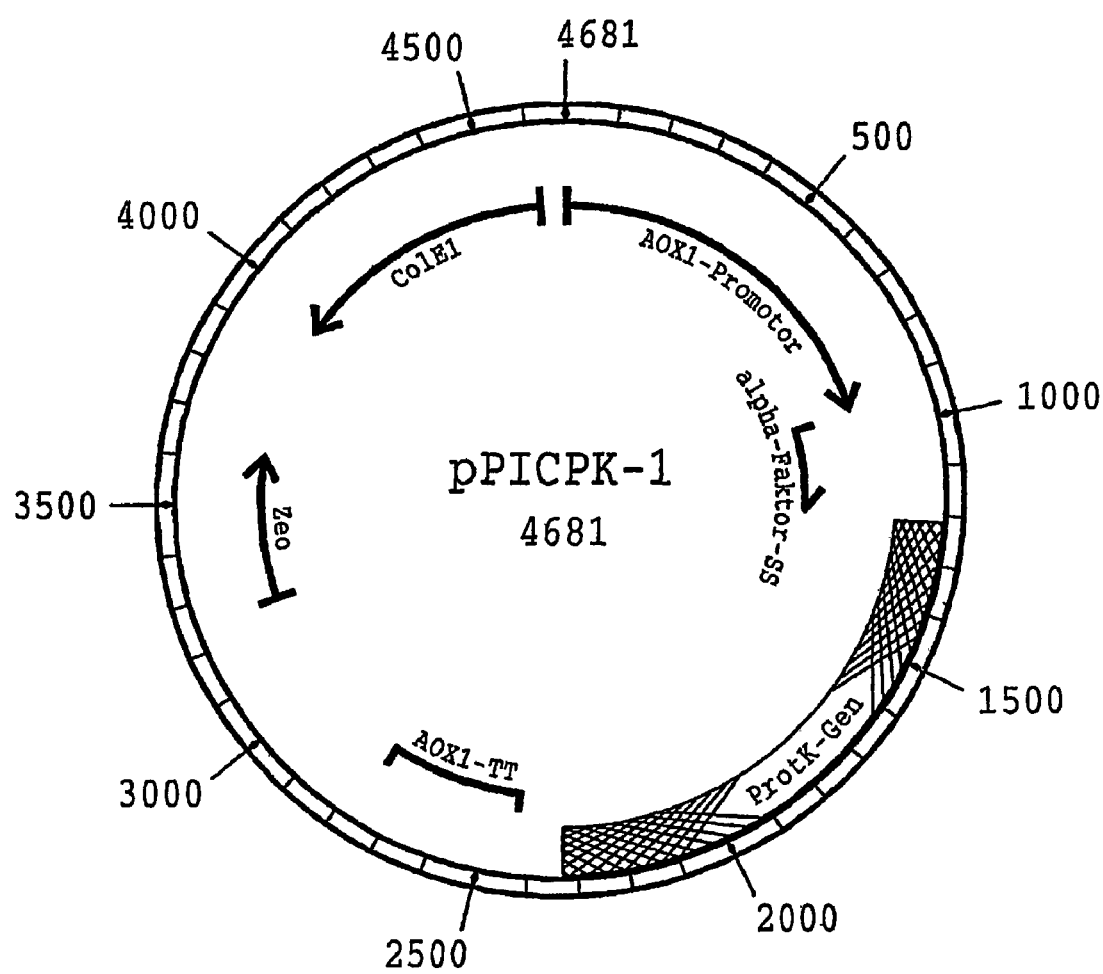
FIG. 1

Expression plasmid pPICPK-1. A sequence coding for the zymogenic proform of proteinase K cloned into the starting vector pPICZαA (Invitrogen).

FIG. 2

Expression plasmid pPICPK-2. A sequence coding for the zymogenic proform of proteinase K cloned into the starting vector pPIC9K (Invitrogen).

EXAMPLES

Example 1

Gene Synthesis

The gene for mature proteinase K from *Tritirachium album* Limber without a signal sequence and without an intron was generated by means of gene synthesis. The sequence (without a native signal peptide) of Gunkel and Gassen, 1989 of 368 amino acids in length was used as a template. A codon-optimized nucleic acid sequence for expression in *E. coli* as well as yeast was obtained by retranslating the amino acid sequence. The amino acid sequence is shown in SEQ ID NO:1 and the nucleotide sequence is shown in SEQ ID NO:2.

For the gene synthesis the gene was divided into 18 fragments of sense and reverse, complementary counter-strand oligonucleotides in alternating sequence (SEQ ID NO: 3-20). An at least 15 bp region was attached to the 5' end and to the 3' end which in each case overlapped the neighbouring oligonucleotides. Recognition sites for restriction endonucleases were attached to the 5' and 3' ends of the synthetic gene outside the coding region for subsequent cloning into expression vectors. The oligonucleotide shown in SEQ ID NO: 3 which contains an EcoRI cleavage site was used as a 5' primer for cloning the pro-proteinase K gene. SEQ ID NO: 20 shows the 3' primer containing a HindIII cleavage site. The 3' primer contains an additional stop codon after the natural stop codon to ensure termination of the translation.

The oligonucleotides were linked together by means of a PCR reaction and the resulting gene was amplified. For this the gene was firstly divided into three fragments of 6 oligonucleotides each and the three fragments were linked together in a second PCR cycle.

Fragment 1 is composed of the oligonucleotides shown in SEQ ID NO: 3-8, fragment 2 is composed of the oligonucleotides shown in SEQ ID NO: 9-14 and fragment 3 is composed of the oligonucleotides shown in SEQ ID NO: 15-20.

The following PCR parameters were applied PCR Reaction 1 (Generation of Three Fragments)

| 5 min   | 95° C. | hot start       |
|---------|--------|-----------------|
| 2 min   | 95° C. |                 |
| 2 min   | 42° C. | } 30 cycles     |
| 1.5 min | 72° C. |                 |
| 7 min   | 72° C. | final extension |

PCR Reaction 2 (Linkage of the Fragments to Form the Total Gene)

| 5 min   | 95° C. | hot start                          |
|---------|--------|------------------------------------|
| 1.5 min | 95° C. |                                    |
| 2 min   | 48° C. | } 6 cycles (without terminal primers) |
| 2 min   | 72° C. |                                    | addition of terminal primers

| 1.5 min | 95° C. | } 25 cycles (with terminal primers) |
|---------|--------|--------------------------------------|
| 1.5 min | 60° C. |                                      |

-continued

| 2 min | 72° C. | |
| 7 min | 72° C. | final extension |

Example 2

Cloning of the Synthetic Proteinase K Fragment from the Gene Synthesis

The PCR mixture was applied to an agarose gel and the ca. 1130 bp PCR fragment was isolated from the agarose gel (Geneclean II Kit from Bio 101, Inc. CA USA). The fragment was cleaved for 1 hour at 37° C. with the EcoRI and HindIII restriction endonucleases (Roche Diagnostics GmbH, Germany). At the same time the pUC18 plasmid (Roche Diagnostics GmbH, Germany) was cleaved for 1 hour at 37° C. with the EcoRI and HindIII restriction endonucleases, the mixture was separated by agarose gel electrophoresis and the 2635 bp vector fragment was isolated. Subsequently the PCR fragment and the vector fragment were ligated together using T4 DNA ligase. For this 1 µl (20 ng) vector fragment and 3 µl (100 ng) PCR fragment, 1 µl 10× ligase buffer (Maniatis et al., 1989, B.27), 1 µl T4 DNA ligase, 4 µl sterile redistilled $H_2O$ were pipetted, carefully mixed and incubated overnight at 16° C.

The cloned gene was examined by restriction analysis and by multiple sequencing of both strands.

Example 3

Vector Construction

The synthetic gene has to be firstly isolated again from the pUC plasmid. For this purpose 1 µg plasmid DNA was firstly incubated with the restriction endonuclease HindIII (Roche Diagnostics GmbH) according to the manufacturer's instructions and subsequently the restriction endonuclease was inactivated by heating to 65° C. for 20 min. Afterwards the resulting DNA overhangs were filled in with Klenow polymerase according to the manufacturer's instructions (Roche Diagnostics GmbH) and the Klenow polymerase was then inactivated by incubating at 75° C. for 10 min. Finally the vector fragment which was now linearized of the above-mentioned pUC plasmid was cleaved with the restriction endonuclease EcoRI (Roche Diagnostics GmbH) according to the manufacturer's instructions, the reaction mixture was applied to a 1% agarose gel and the fragments were separated according to size by applying a current (100 V/150 mA). The ca. 1120 bp fragment containing the gene for pro-proteinase K (ppk gene) was isolated from the agarose gel (QIAquick Gel Extraction Kit/Qiagen).

The vector pPICZαA (Invitrogen) was cleaved with the restriction endonuclease Asp718I (Roche Diagnostics GmbH) according to the manufacturer's instructions and the restriction endonuclease was inactivated by heating the incubation mixture to 65° C. for 20 min. Afterwards the resulting DNA overhangs were filled in with Klenow polymerase according to the manufacturer's instructions (Roche Diagnostics GmbH) and the Klenow polymerase was then inactivated by incubating at 75° C. for 10 min. Finally the vector fragment which was now linearized of pPICZαA was cleaved with the restriction endonuclease EcoRI (Roche Diagnostics GmbH) according to the manufacturer's instructions, the reaction mixture was applied to a 1% agarose gel and the fragments were separated according to size by applying a current (100 V/150 mA). The ca. 3550 bp vector fragment was isolated from the agarose gel (QIAquick Gel Extraction Kit/Qiagen).

The fragments obtained in this manner were ligated together by standard methods (Sambrook et al. 1989). In this vector the ppk gene is under the control of the AOX-1 promoter (promoter for alcohol oxidase 1 from Pichia pastoris, inducible with methanol) and is cloned using this cloning strategy in the correct reading frame behind the signal peptide of the α-factor from Saccharomyces cerevisiae. The gene fragment inserted in this manner was then examined for an error free sequence by means of restriction analysis and sequencing. The resulting expression vector which contains the ppk gene which codes for pro-proteinase K was named pPICPK-1 (see FIG. 1).

Subsequently the ppk gene was also cloned into pPIC9K (Invitrogen). For this purpose the vector pPICPK-1 was cleaved according to the manufacturer's instructions with the restriction endonucleases PmeI and NotI (Roche Diagnostics GmbH), the fragments from the restriction mixture were separated according to size in a 1% agarose gel and the ca. 1960 bp fragment containing the 3' part of the AOX1-promoter region, the sequence for the signal peptide of the α-factor and the ppk gene was isolated from the gel (QIAquick Gel Extraction Kit/Qiagen). At the same time the vector pPIC9K was cleaved with the restriction endonucleases PmeI and NotI (Roche Diagnostics GmbH) according to the manufacturer's instructions, the fragments from the restriction mixture were separated according to size in a 1% agarose gel and the ca. 8450 bp vector fragment was isolated from the gel (QIAquick Gel Extraction Kit/Qiagen).

Subsequently the fragments obtained in this manner were ligated together by standard methods (Sambrook et al. 1989). In this vector the ppk gene is also under the control of the AOX1-promoter (promoter for the alcohol oxidase 1 from Pichia pastoris, inducible with methanol). The vector pPIC9K differs from the vector pPICZαA by the selection marker and by three possibilities known to a person skilled in the art for integrating it into the Pichia genome depending on the vector linearization before transformation whereas the integration of pPICZαA into the AOX1-locus is fixed. The inserted gene fragment was then examined for an error-free sequence by means of restriction analysis and sequencing.

Figure 2:
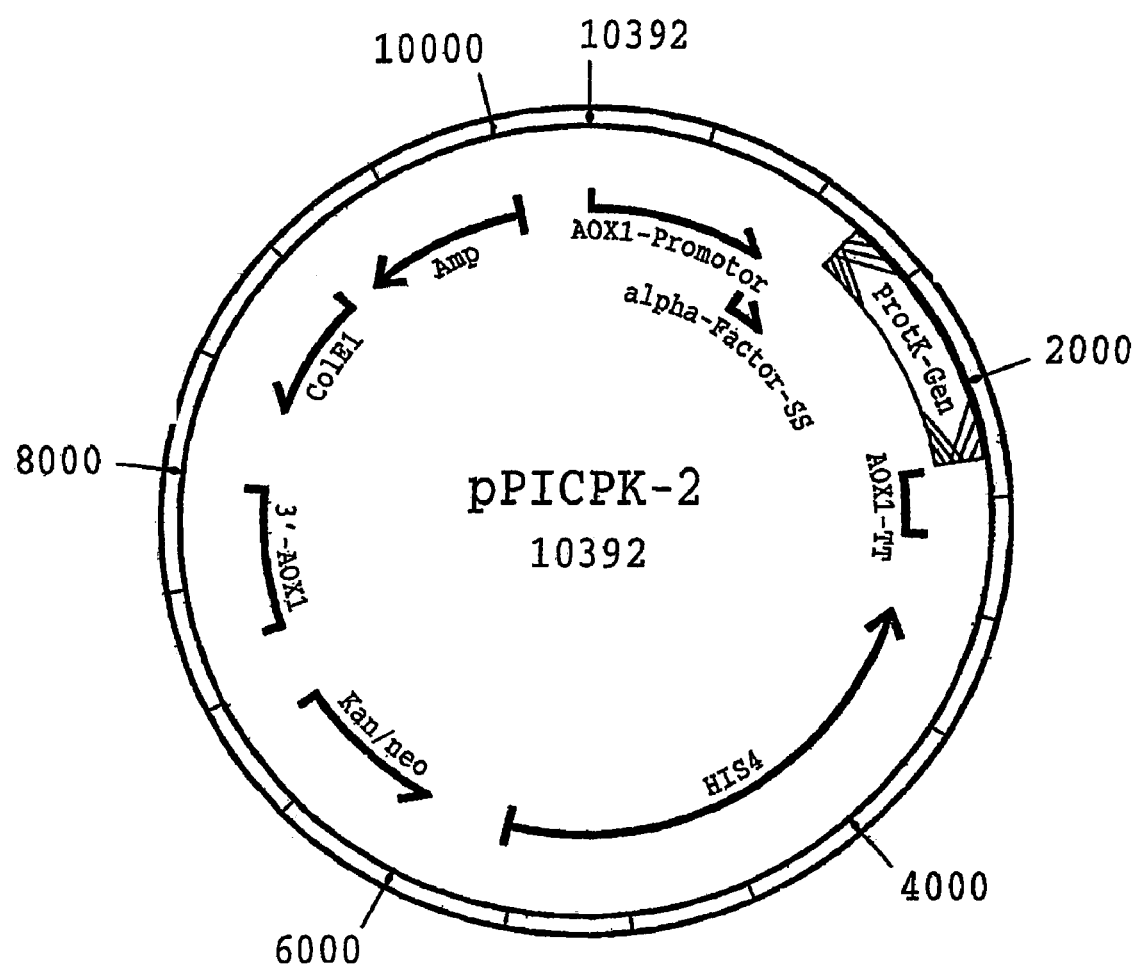

The resulting expression vector which contains the ppk gene which codes for pro-proteinase K was named pPICPK-2 (see FIG. 2).

Example 4

Transformation of pPICPK-1 in Pichia pastoris

In order to transform pPICPK-1 in Pichia pastoris X-33 with subsequent integration into the genome, the vector was firstly linearized with PmeI (Roche Diagnostics GmbH). The transformation was carried out by means of electroporation using a Gene Pulser II (Biorad).

For this purpose 5 ml YPD medium (according to the Invitrogen catalogue) was inoculated with a colony of Pichia pastoris wild-type strain and incubated overnight at 30° C. while shaking. The overnight culture was subsequently reinoculated 1:2000 in 200 ml fresh YPD medium (according to the Invitrogen catalogue) and incubated overnight at 30° C. while shaking until the $OD_{600}$ reached 1.3-1.5. The cells were centrifuged (1500×g/5 minutes) and the pellet was resuspended in 200 ml ice-cold sterile water (0° C.). The cells were again centrifuged (1500×g/5 minutes) and resuspended in 100 ml ice-cold sterile water (0° C.). The cells were again centrifuged and resuspended in 10 ml ice-cold (0° C.) 1 M sorbitol (ICN). The cells were again centrifuged and resuspended in 0.5 ml ice-cold (0° C.) 1 M sorbitol (ICN). The cells obtained in this manner were kept on ice and used immediately for transformation.

About 1 µg linearized pPICPK-1 vector DNA was added to 80 µl of the cells and the entire mixture was transferred to an ice-cold (0° C.) electroporation cuvette and incubated for a further 5 minutes on ice. Subsequently the cuvette was transferred to a Gene Pulser II (Biorad) and the transformation was carried out at 1 kV, 1 kΩ and 25 µF. After electroporation 1 ml 1 M sorbitol (ICN) was added to the mixture and subsequently 100-150 µl was plated out on a YPDS agar plate (according to the Invitrogen catalogue) containing 100 µg/ml Zeocin® (Invitrogen). The plates were subsequently incubated for 2-4 days at 30° C.

Minimal dextrose grid plates were inoculated with the clones and the clones were analysed further.

Clones that had grown were picked, resuspended in 20 µl sterile water and lysed with 17.5 U lyticase (Roche Diagnostics GmbH) (1 hour, 37° C.) and examined directly by means of PCR for the correct integration of the ppk expression cassette.

Clones which had integrated the complete expression cassette during transformation into the genome were then used in expression experiments.

Example 5

Transformation of pPICPK-2 in *Pichia pastoris*

In order to transform pICPK-2 in *Pichia pastoris* GS115 with subsequent integration into the genome, the vector was firstly linearized for variant I with PmeI (Roche Diagnostics GmbH) to integrate it into the AOXI-locus and linearized with SalI (Roche Diagnostics GmbH) for variant II to integrate it into the His4 locus. The transformation was carried out by means of electroporation using a Gene Pulser (Biorad).

For this purpose 5 ml YPD medium (according to the Invitrogen catalogue) was inoculated with a colony of *Pichia pastoris* GS115 wild-type strain and incubated overnight at 30° C. while shaking. The overnight culture was subsequently reinoculated 1:2000 in 200 ml fresh YPD medium (according to the Invitrogen catalogue) and incubated overnight at 30° C. while shaking until the $OD_{600}$ reached 1.3-1.5. The cells were centrifuged (1500×g/5 minutes) and the pellet was resuspended in 200 ml ice-cold sterile water (0° C.). The cells were again centrifuged (1500×g/5 minutes) and resuspended in 100 ml ice-cold sterile water (0° C.). The cells were again centrifuged and resuspended in 10 ml ice-cold (0° C.) 1 M sorbitol (ICN). The cells were again centrifuged and resuspended in 0.5 ml ice-cold (0° C.) 1 M sorbitol (ICN). The cells obtained in this manner were kept on ice and used immediately for transformation.

About 1 µg linearized pPICPK-2 vector DNA was added to 80 µl of the cells and the entire mixture was transferred to an ice-cold (0° C.) electroporation cuvette and incubated for a further 5 minutes on ice. Subsequently the cuvette was transferred to a Gene Pulser II (Biorad) and the transformation was carried out at 1 kV, 1 kΩ and 25 µF. After electroporation 1 ml 1 M sorbitol (ICN) was added to the mixture and subsequently 100-150 µl was plated out on a MM agar plate (minimal medium according to the Invitrogen catalogue) without histidine. The plates were subsequently incubated for 2-4 days at 30° C. Clones of *Pichia pastoris* GS115 which have a defective His4 gene caused by mutation (histidinol dehydrogenase) can only grow on these plates when they have integrated the vector pPICPK-2 which has a functional His4 gene as an insert and can hence compensate the deficiency in histidine biosynthesis.

Minimal dextrose grid plates were inoculated with the clones and the clones were analysed further. Clones that had grown were picked, resuspended in 20 µl sterile water and lysed with 17.5 U lyticase (Roche Diagnostics GmbH) (1 hour, 37° C.) and examined directly by means of PCR for the correct integration of the ppk expression cassette.

Clones which had integrated the complete expression cassette during transformation into the genome were then used in expression experiments.

Example 6

Expression of Proteinase K 10 ml BMGY medium (according to the Invitrogen catalogue) was inoculated with positive clones and incubated overnight at 30° C. while shaking. Subsequently the optical density at 600 nm was determined and 10 ml BMMY medium (according to the Invitrogen catalogue) was inoculated in such a manner that an $OD_{600}$ of 1 resulted. The BMMY medium (according to the Invitrogen catalogue) contains methanol (Mallinckrodt Baker B.V) which induces the expression of proteinase K via the AOX1 promoter.

The shaking flask was incubated at 30° C. while shaking, samples were taken every 24 hours, the $OD_{600}$ was determined, an activity test was carried out for expression of proteinase K and each time 0.5% methanol (Mallinckrodt Baker B.V) was refed for further induction. The expression experiments ran for 168 hours.

Example 7

Activity Test for Secreted Recombinant Proteinase K

For the activity test for recombinant proteinase K one requires $CaCl_2 \times 2H_2O$ (Merck ID-No. 102382), DMSO (Merck, ID-No. 109678), the substrate Suc-Ala-Ala-Pro-Phe-pNA (Roche Diagnostics ID-No. 0716766) and Tris base (Roche Diagnostics ID-No. 0153265).

The composition of the solutions was as follows:
Solution 1: 50 mmol/l Tris-Base; 10 mmol/l $CaCl_2$ pH 8.2
Solution 2: 125 mg Suc-Ala-Ala-Pro-Phe-pNA dissolved in 1 ml DMSO The cells were centrifuged (5 min 10000 rpm Eppendorf bench centrifuge) and the supernatant was diluted 1:500 in solution 1.

2 ml of solution 1 was pipetted into a cuvette and 0.02 ml of solution 2 was added. Both solutions were mixed and incubated at a reaction temperature of 25° C. The reaction was started by adding 0.05 ml of the diluted supernatant as stated above and remixing, the change in absorbance at 405 nm was measured and the ΔA/min in the linear region was measured. The following formula was then used for the calculation:

$$\text{activity} = \frac{2.07}{\epsilon \times 1 \times 0.05} \Delta A/\text{min} [U/\text{ml sample solution}]$$

2.07=sample volume
$\epsilon_{405}$=10.4 [$mmol^{-1} \times l \times cm^{-1}$]
1=path length of the cuvette
0.05=volume of the added sample

The invention claimed is:

1. A method for producing recombinant proteinase K comprising:
   (a) transforming a *Pichia pastoris* yeast cell with a vector construct comprising a DNA sequence encoding a signal peptide fused upstream of a DNA sequence encoding a zymogenic precursor of proteinase K, and additional sequences that place the zymogenic precursor coding sequence under the control of a promoter for the host cell,
   (b) expressing the zymogenic precursor of proteinase K, and
   (c) secreting and autocatalytically activating the zymogenic precursor to produce said recombinant proteinase K,
   wherein the proteinase K is secreted in soluble form, and the yeast cells continue to grow during recombinant proteinase K expression and secretion, without a detectable increase in yeast cell lysis.

2. The method of claim 1 wherein the DNA sequence encoding the zymogenic precursor of proteinase K is cloned into a vector selected from the group consisting of pPICZ, pPICZα, pGAPZ, pGAPZα, pPICZαA, and pPIC9K.

3. The method of claim 1 wherein the expressing of the zymogenic precursor of proteinase K is induced by methanol.

4. The method of claim 1 wherein the vector construct comprises a nucleic acid sequence encoding the signal peptide of α-factor from *Saccharomyces cerevisiae*.

5. The method of claim 1 wherein the vector is pPICZαA and the promoter is AOXI.

6. A method for producing recombinant proteinase K comprising
   expressing a zymogenic precursor of proteinase K in a *Pichia pastoris* yeast cell, said yeast cell comprising a vector construct comprising a DNA sequence encoding a signal peptide fused upstream of a DNA sequence encoding a zymogenic precursor of proteinase K, and additional sequences that place the zymogenic precursor coding sequence under the control of a promoter for the yeast cell,
   secreting and autocatalytically activating the zymogenic precursor to produce said recombinant proteinase K, wherein the proteinase K is secreted in soluble form, and the yeast cells continue to grow during recombinant proteinase K expression and secretion, without a detectable increase in yeast cell lysis.

7. The method of claim 1 wherein the vector is selected from the group consisting of pPICZα and pPIC9K.

8. The method of claim 1 wherein the DNA sequence coding for a zymogenic precursor of proteinase K comprises the sequence of SEQ ID NO: 2.

* * * * *

SEQUENCE LISTING

<160> NUMBER OF SEQ ID NOS: 21

<210> SEQ ID NO 1
<211> LENGTH: 369
<212> TYPE: PRT
<213> ORGANISM: Tritirachium album Limber

<400> SEQUENCE: 1

```
Ala Pro Ala Val Glu Gln Arg Ser Glu Ala Ala Pro Leu Ile Glu Ala
 1               5                  10                  15

Arg Gly Glu Met Val Ala Asn Lys Tyr Ile Val Lys Phe Lys Glu Gly
                20                  25                  30

Ser Ala Leu Ser Ala Leu Asp Ala Ala Met Glu Lys Ile Ser Gly Lys
            35                  40                  45

Pro Asp His Val Tyr Lys Asn Val Phe Ser Gly Phe Ala Ala Thr Leu
 50                  55                  60

Asp Glu Asn Met Val Arg Val Leu Arg Ala His Pro Asp Val Glu Tyr
 65                  70                  75                  80

Ile Glu Gln Asp Ala Val Val Thr Ile Asn Ala Ala Gln Thr Asn Ala
                85                  90                  95

Pro Trp Gly Leu Ala Arg Ile Ser Ser Thr Ser Pro Gly Thr Ser Thr
            100                 105                 110

Tyr Tyr Tyr Asp Glu Ser Ala Gly Gln Gly Ser Cys Val Tyr Val Ile
            115                 120                 125

Asp Thr Gly Ile Glu Ala Ser His Pro Glu Phe Glu Gly Arg Ala Gln
130                 135                 140

Met Val Lys Thr Tyr Tyr Ser Ser Arg Asp Gly Asn Gly His Gly
145                 150                 155                 160

Thr His Cys Ala Gly Thr Val Gly Ser Arg Thr Tyr Gly Val Ala Lys
                165                 170                 175

Lys Thr Gln Leu Phe Gly Val Lys Val Leu Asp Asp Asn Gly Ser Gly
            180                 185                 190

Gln Tyr Ser Thr Ile Ile Ala Gly Met Asp Phe Val Ala Ser Asp Lys
        195                 200                 205

Asn Asn Arg Asn Cys Pro Lys Gly Val Val Ala Ser Leu Ser Leu Gly
210                 215                 220

Gly Gly Tyr Ser Ser Ser Val Asn Ser Ala Ala Ala Arg Leu Gln Ser
225                 230                 235                 240

Ser Gly Val Met Val Ala Val Ala Ala Gly Asn Asn Ala Asp Ala
                245                 250                 255

Arg Asn Tyr Ser Pro Ala Ser Glu Pro Ser Val Cys Thr Val Gly Ala
            260                 265                 270

Ser Asp Arg Tyr Asp Arg Arg Ser Ser Phe Ser Asn Tyr Gly Ser Val
        275                 280                 285

Leu Asp Ile Phe Gly Pro Gly Thr Ser Ile Leu Ser Thr Trp Ile Gly
290                 295                 300

Gly Ser Thr Arg Ser Ile Ser Gly Thr Ser Met Ala Thr Pro His Val
305                 310                 315                 320

Ala Gly Leu Ala Ala Tyr Leu Met Thr Leu Gly Lys Thr Thr Ala Ala
                325                 330                 335

Ser Ala Cys Arg Tyr Ile Ala Asp Thr Ala Asn Lys Gly Asp Leu Ser
            340                 345                 350

Asn Ile Pro Phe Gly Thr Val Asn Leu Leu Ala Tyr Asn Asn Tyr Gln
```

355        360        365
Ala

<210> SEQ ID NO 2
<211> LENGTH: 1124
<212> TYPE: DNA
<213> ORGANISM: Tritirachium album Limber

<400> SEQUENCE: 2

```
gaattcgctc ctgccgttga gcagcgctcc gaggctgctc ctctgatcga ggcccgcggc    60
gagatggttg ccaacaagta catcgtcaag ttcaaggagg gtagcgctct ttccgctctg   120
gatgctgcca tggagaagat ctctggcaag cccgaccacg tctacaagaa cgtcttcagc   180
ggtttcgctc gaccctgga cgagaacatg gttcgggttc ccgcgccca ccccgatgtt    240
gagtacatcg agcaggatgc tgttgtcacc atcaacgctg cgcagaccaa cgctccctgg   300
ggcctggctc gcatctccag caccagcccc ggtacctcta cctactacta tgacgaatct   360
gccggccaag gctcctgcgt ctacgtgatc gacaccggta tcgaggcatc gcaccccgag   420
ttcgagggtc gtgcccagat ggtcaagacc tactactact ccagtcgcga cggtaacggt   480
cacggcaccc actgcgctgg taccgttggc tcccgtacct acggtgtcgc caagaagacc   540
cagctgttcg gtgtcaaggt cctggatgac aacggcagtg ccagtactc caccatcatc   600
gccggtatgg acttcgttgc cagcgacaag aacaaccgca actgccccaa aggtgtcgtt   660
gcctccttat ccctgggcgg tggttactcc tcctccgtga cagcgccgc tgcccgcctc   720
cagagctctg gtgtcatggt cgccgtcgct gccggtaaca caacgctga cgcccgcaac   780
tactcccctg cttctgagcc ctcggtctgc accgtcggtg cttctgaccg ctacgaccgc   840
cgctccagct tctccaacta cggcagcgtt ttggacatct tcggccctgg taccagcatc   900
ctctccacct ggatcggcgg cagcacccgc tccatctctg gtacctccat ggctactccc   960
cacgttgccg gtctcgctgc ctacctcatg actcttggaa agactaccgc cgccagcgct  1020
tgccgataca ttgccgacac cgccaacaag ggcgacttaa gcaacattcc cttcggcact  1080
gtcaacttgc ttgcctacaa caactaccag gcttaatgaa gctt                  1124
```

<210> SEQ ID NO 3
<211> LENGTH: 79
<212> TYPE: DNA
<213> ORGANISM: Artificial Sequence
<220> FEATURE:
<223> OTHER INFORMATION: Description of Artificial Sequence: Primer

<400> SEQUENCE: 3

```
cgcgaattcg ctcctgccgt tgagcagcgc tccgaggctg ctcctctgat cgaggcccgc    60
ggcgagatgg ttgccaaca                                                79
```

<210> SEQ ID NO 4
<211> LENGTH: 80
<212> TYPE: DNA
<213> ORGANISM: Artificial Sequence
<220> FEATURE:
<223> OTHER INFORMATION: Description of Artificial Sequence: Primer

<400> SEQUENCE: 4

```
atcttctcca tggcagcatc cagagcggaa agagcgctac cctccttgaa cttgacgatg    60
tacttgttgg caaccatctc                                                80
```

```
<210> SEQ ID NO 5
<211> LENGTH: 80
<212> TYPE: DNA
<213> ORGANISM: Artificial Sequence
<220> FEATURE:
<223> OTHER INFORMATION: Description of Artificial Sequence: Primer

<400> SEQUENCE: 5
tgccatggag aagatctctg gcaagcccga ccacgtctac aagaacgtct tcagcggttt      60
cgctgcgacc ctggacgaga                                                  80

<210> SEQ ID NO 6
<211> LENGTH: 64
<212> TYPE: DNA
<213> ORGANISM: Artificial Sequence
<220> FEATURE:
<223> OTHER INFORMATION: Description of Artificial Sequence: Primer

<400> SEQUENCE: 6
tgctcgatgt actcaacatc ggggtgggcg cggagaaccc gaaccatgtt ctcgtccagg      60
gtcg                                                                   64

<210> SEQ ID NO 7
<211> LENGTH: 65
<212> TYPE: DNA
<213> ORGANISM: Artificial Sequence
<220> FEATURE:
<223> OTHER INFORMATION: Description of Artificial Sequence: Primer

<400> SEQUENCE: 7
tgagtacatc gagcaggatg ctgttgtcac catcaacgct gcgcagaccg ctgcgcagac      60
caacg                                                                  65

<210> SEQ ID NO 8
<211> LENGTH: 70
<212> TYPE: DNA
<213> ORGANISM: Artificial Sequence
<220> FEATURE:
<223> OTHER INFORMATION: Description of Artificial Sequence: Primer

<400> SEQUENCE: 8
agtaggtaga ggtaccgggg ctggtgctgg agatgcgagc caggccccag ggagcgttgg      60
tctgcgcagc                                                             70

<210> SEQ ID NO 9
<211> LENGTH: 80
<212> TYPE: DNA
<213> ORGANISM: Artificial Sequence
<220> FEATURE:
<223> OTHER INFORMATION: Description of Artificial Sequence: Primer

<400> SEQUENCE: 9
gtacctctac ctactactat gacgaatctg ccggccaagg ctcctgcgtc tacgtgatcg      60
acaccggtat cgaggcatcg                                                  80

<210> SEQ ID NO 10
<211> LENGTH: 81
<212> TYPE: DNA
<213> ORGANISM: Artificial Sequence
<220> FEATURE:
<223> OTHER INFORMATION: Description of Artificial Sequence: Primer

<400> SEQUENCE: 10
```

```
ttaccgtcgc gactggagta gtagtaggtc ttgaccatct gggcacgacc ctcgaactcg    60
gggtgcgatg cctcgatacc g                                              81
```

<210> SEQ ID NO 11
<211> LENGTH: 78
<212> TYPE: DNA
<213> ORGANISM: Artificial Sequence
<220> FEATURE:
<223> OTHER INFORMATION: Description of Artificial Sequence: Primer

<400> SEQUENCE: 11

```
ccagtcgcga cggtaacggt cacggcaccc actgcgctgg taccgttggc tcccgtacct    60
acggtgtcgc caagaaga                                                  78
```

<210> SEQ ID NO 12
<211> LENGTH: 73
<212> TYPE: DNA
<213> ORGANISM: Artificial Sequence
<220> FEATURE:
<223> OTHER INFORMATION: Description of Artificial Sequence: Primer

<400> SEQUENCE: 12

```
atggtggagt actggccact gccgttgtca tccaggacct tgacaccgaa cagctgggtc    60
ttcttggcga cac                                                       73
```

<210> SEQ ID NO 13
<211> LENGTH: 81
<212> TYPE: DNA
<213> ORGANISM: Artificial Sequence
<220> FEATURE:
<223> OTHER INFORMATION: Description of Artificial Sequence: Primer

<400> SEQUENCE: 13

```
ggccagtact ccaccatcat cgccggtatg gacttcgttg ccagcgacaa gaacaaccgc    60
aactgcccca aggtgtcgt t                                               81
```

<210> SEQ ID NO 14
<211> LENGTH: 81
<212> TYPE: DNA
<213> ORGANISM: Artificial Sequence
<220> FEATURE:
<223> OTHER INFORMATION: Description of Artificial Sequence: Primer

<400> SEQUENCE: 14

```
gctctggagg cgggcagcgg cgctgttcac ggaggaggag taaccaccgc ccagggataa    60
ggaggcaacg acacctttgg g                                              81
```

<210> SEQ ID NO 15
<211> LENGTH: 82
<212> TYPE: DNA
<213> ORGANISM: Artificial Sequence
<220> FEATURE:
<223> OTHER INFORMATION: Description of Artificial Sequence: Primer

<400> SEQUENCE: 15

```
gcccgcctcc agagctctgg tgtcatggtc gccgtcgctg ccggtaacaa caacgctgac    60
gcccgcaact actcccctgc tt                                             82
```

<210> SEQ ID NO 16
<211> LENGTH: 80
<212> TYPE: DNA
<213> ORGANISM: Artificial Sequence

```
<220> FEATURE:
<223> OTHER INFORMATION: Description of Artificial Sequence: Primer

<400> SEQUENCE: 16
gttggagaag ctggagcggc ggtcgtagcg gtcagaagca ccgacggtgc agaccgaggg    60
ctcagaagca ggggagtagt                                                80

<210> SEQ ID NO 17
<211> LENGTH: 83
<212> TYPE: DNA
<213> ORGANISM: Artificial Sequence
<220> FEATURE:
<223> OTHER INFORMATION: Description of Artificial Sequence: Primer

<400> SEQUENCE: 17
ctccagcttc tccaactacg gcagcgtttt ggacatcttc ggccctggta ccagcatcct    60
ctccacctgg atcggcggca gca                                            83

<210> SEQ ID NO 18
<211> LENGTH: 81
<212> TYPE: DNA
<213> ORGANISM: Artificial Sequence
<220> FEATURE:
<223> OTHER INFORMATION: Description of Artificial Sequence: Primer

<400> SEQUENCE: 18
tcatgaggta ggcagcgaga ccggcaacgt ggggagtagc catggaggta ccagagatgg    60
agcgggtgct gccgccgatc c                                              81

<210> SEQ ID NO 19
<211> LENGTH: 81
<212> TYPE: DNA
<213> ORGANISM: Artificial Sequence
<220> FEATURE:
<223> OTHER INFORMATION: Description of Artificial Sequence: Primer

<400> SEQUENCE: 19
ctgcctacct catgacctta ggaaagacca ccgccgccag cgcttgccgt tacatcgccg    60
acaccgccaa caagggcgac t                                              81

<210> SEQ ID NO 20
<211> LENGTH: 87
<212> TYPE: DNA
<213> ORGANISM: Artificial Sequence
<220> FEATURE:
<223> OTHER INFORMATION: Description of Artificial Sequence: Primer

<400> SEQUENCE: 20
atataagctt ctattaagcc tggtagttgt tgtaggctaa caggttgacg gtgccgaagg    60
gaatgttgct taagtcgccc ttgttgg                                        87

<210> SEQ ID NO 21
<211> LENGTH: 384
<212> TYPE: PRT
<213> ORGANISM: Tritirachium album Limber

<400> SEQUENCE: 21

Met Arg Leu Ser Val Leu Leu Ser Leu Leu Pro Leu Ala Leu Gly Ala
 1               5                  10                  15

Pro Ala Val Glu Gln Arg Ser Glu Ala Ala Pro Leu Ile Glu Ala Arg
            20                  25                  30
```

```
Gly Glu Met Val Ala Asn Lys Tyr Ile Val Lys Phe Lys Glu Gly Ser
         35                  40                  45

Ala Leu Ser Ala Leu Asp Ala Ala Met Glu Lys Ile Ser Gly Lys Pro
 50                  55                  60

Asp His Val Tyr Lys Asn Val Phe Ser Gly Phe Ala Ala Thr Leu Asp
 65                  70                  75                  80

Glu Asn Met Val Arg Val Leu Arg Ala His Pro Asp Val Glu Tyr Ile
                 85                  90                  95

Glu Gln Asp Ala Val Val Thr Ile Asn Ala Ala Gln Thr Asn Ala Pro
                100                 105                 110

Trp Gly Leu Ala Arg Ile Ser Ser Thr Ser Pro Gly Thr Ser Thr Tyr
        115                 120                 125

Tyr Tyr Asp Glu Ser Ala Gly Gln Gly Ser Cys Val Tyr Val Ile Asp
        130                 135                 140

Thr Gly Ile Glu Ala Ser His Pro Glu Phe Glu Gly Arg Ala Gln Met
145                 150                 155                 160

Val Lys Thr Tyr Tyr Ser Ser Arg Asp Gly Asn Gly His Gly Thr
                165                 170                 175

His Cys Ala Gly Thr Val Gly Ser Arg Thr Tyr Gly Val Ala Lys Lys
                180                 185                 190

Thr Gln Leu Phe Gly Val Lys Val Leu Asp Asp Asn Gly Ser Gly Gln
        195                 200                 205

Tyr Ser Thr Ile Ile Ala Gly Met Asp Phe Val Ala Ser Asp Lys Asn
210                 215                 220

Asn Arg Asn Cys Pro Lys Gly Val Val Ala Ser Leu Ser Leu Gly Gly
225                 230                 235                 240

Gly Tyr Ser Ser Ser Val Asn Ser Ala Ala Ala Arg Leu Gln Ser Ser
                245                 250                 255

Gly Val Met Val Ala Val Ala Ala Gly Asn Asn Asn Ala Asp Ala Arg
                260                 265                 270

Asn Tyr Ser Pro Ala Ser Glu Pro Ser Val Cys Thr Val Gly Ala Ser
        275                 280                 285

Asp Arg Tyr Asp Arg Arg Ser Ser Phe Ser Asn Tyr Gly Ser Val Leu
        290                 295                 300

Asp Ile Phe Gly Pro Gly Thr Ser Ile Leu Ser Thr Trp Ile Gly Gly
305                 310                 315                 320

Ser Thr Arg Ser Ile Ser Gly Thr Ser Met Ala Thr Pro His Val Ala
                325                 330                 335

Gly Leu Ala Ala Tyr Leu Met Thr Leu Gly Lys Thr Thr Ala Ala Ser
                340                 345                 350

Ala Cys Arg Tyr Ile Ala Asp Thr Ala Asn Lys Gly Asp Leu Ser Asn
        355                 360                 365

Ile Pro Phe Gly Thr Val Asn Leu Leu Ala Tyr Asn Asn Tyr Gln Ala
370                 375                 380
```